(12) United States Patent
Tirouvanziam (10) Patent No.: US 11,280,783 B2
(45) Date of Patent: Mar. 22, 2022

(54) DEVICES AND METHODS RELATED TO AIRWAY INFLAMMATION

(71) Applicants: Emory University, Atlanta, GA (US); Children's Healthcare of Atlanta, Inc., Atlanta, GA (US)

(72) Inventor: Rabindra M. Tirouvanziam, Decatur, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 16/862,366

(22) Filed: Apr. 29, 2020

(65) Prior Publication Data

US 2020/0256866 A1    Aug. 13, 2020

Related U.S. Application Data

(63) Continuation of application No. 14/913,543, filed as application No. PCT/US2014/052048 on Aug. 21, 2014, now Pat. No. 10,670,594.

(Continued)

(51) Int. Cl.
*G01N 33/543* (2006.01)
*G01N 33/50* (2006.01)
(Continued)

(52) U.S. Cl.
CPC ....... *G01N 33/54366* (2013.01); *G01N 33/15* (2013.01); *G01N 33/50* (2013.01);
(Continued)

(58) Field of Classification Search
CPC .. G01N 33/54366; G01N 33/15; G01N 33/50; G01N 33/5047; G01N 33/5082;
(Continued)

(56) References Cited

U.S. PATENT DOCUMENTS 10,670,594 B2    6/2020    Tirovanziam
2010/0047907 A1   2/2010   Li

OTHER PUBLICATIONS

Tirouvanziam et al. Profound functional and signaling changes in viable inflammatory neutrophils homing cystic fibrosis airways. PNAS 105 (11): 4335-4339 (Mar. 18, 2008).*

(Continued)

*Primary Examiner* — Gailene Gabel
(74) *Attorney, Agent, or Firm* — Emory Patent Group (57) ABSTRACT

This disclosure relates to devices, assays, and methods related to airway inflammation caused by polymorphonuclear neutrophils (PMNs). In certain embodiments, the disclosure relates to a model device that emulates the changes in airway cell physiology due to transmigration of PMNs from blood to the cells at the air-liquid interface. In certain embodiments, the airway cells are supported on a collagen layer wherein the collagen layer is further supported by a porous polymer from which PMNs can migrate. In certain embodiments, the disclosure contemplates adding bacteria, fungi and/or viruses to the device to emulate disease states. In certain embodiments, the disclosure relates to the use of the model system to test compounds to identify drug candidates and diagnose subjects with airway-related diseases and conditions.

4 Claims, 6 Drawing Sheets

Related U.S. Application Data (60) Provisional application No. 61/868,722, filed on Aug. 22, 2013.

(51) Int. Cl.
    *G01N 33/68*     (2006.01)
    *G01N 33/15*     (2006.01)
    *G01N 33/569*     (2006.01)

(52) U.S. Cl.
    CPC ..... *G01N 33/5047* (2013.01); *G01N 33/5082* (2013.01); *G01N 33/56972* (2013.01); *G01N 33/6887* (2013.01); *G01N 2333/78* (2013.01); *G01N 2500/10* (2013.01); *G01N 2800/12* (2013.01); *G01N 2800/122* (2013.01); *G01N 2800/7052* (2013.01)

(58) Field of Classification Search
    CPC ........... G01N 33/6887; G01N 2333/78; G01N 2500/10; G01N 2800/12; G01N 2800/122; G01N 2800/7052; G01N 33/56972
See application file for complete search history.

(56) References Cited

OTHER PUBLICATIONS

Kato et al. Airway epithelial cells promote transmigration of eosinophils in a new three-dimensional chemotaxis model. Clinical and Experimental Allergy. 32 (6): 889-897 (2002).*
Conese et al. Neutrophil recruitment and airway epithelial cell involvement in chronic cystic fibrosis lung disease, Journal of Cystic Fibrosis, 2 (2003) 129-135.
Damian et al. An Air-Liquid Interface Culture System For Small Airway Epithelial Cells, C74 Acute Lung Injury: Diverse Novel Insights / Thematic Poster Session / Tuesday, May 17/8:15 AM-4:30 PM, (2011).
Downey et al. Neutrophils in cystic fibrosis,Thorax 2009, 64:81-88.
Forrest et al. Frontline Science: Pathological conditioning of human neutrophils recruited to the airwaymilieu in cystic fibrosis, J LeukocBiol. 2018, 104:665-675.
Fulcher et al. Well-Differentiated Human Airway Epithelial Cell Cultures, Chapter 13, Methods in Molecular Medicine, vol. 107: Human Cell Culture, 183-206, 2005.
Gernez et al. Modulation of mTOR Effector Phosphoproteins in Blood Basophils from Allergic Patients, J Clin Immunol (2012) 32:565-573.
Ghio et al. Growth of human bronchial epithelial cells at an air-liquid interface alters the response to particle exposure, Particle and Fibre Toxicology, 2013, 10:25.
Grunwell et al. Neutrophil Dysfunction in the Airways of Children with Acute Respiratory Failure Due to Lower Respiratory Tract Viral and Bacterial Coinfections, Scientific Reports, (2019) 9:2874.
Ingersoll et al. Mature Cystic Fibrosis Airway Neutrophils Suppress T Cell Function: Evidence for a Role of Arginase 1 but Not Programmed Death-Ligand 1, The Journal of Immunology, 2015, 194: 5520-5528.
Karp et al. An In Vitro Model of Differentiated Human Airway Epithelia, Chapter 11,Methods in Molecular Biology, vol. 188: Epithelial Cell Culture Protocols Edited by: C. Wise © Humana Press Inc., Totowa, NJ, pp. 115-137, (2002).
Kato et al. Airway epithelial cells promote transmigration of eosinophils in a new three-dimensional chemotaxis model, Clin Exp Allergy, 2002, 32:889-897.
Knight et al. Alvetex®: Polystyrene Scaffold Technology for Routine Three Dimensional Cell Culture, Chapter 20, John W. Haycock (ed.), 3D Cell Culture: Methods and Protocols, Methods in Molecular Biology, vol. 695, 323-340, (2011).
Laval et al. Metabolic Adaptation of Neutrophils in Cystic Fibrosis Airways Involves Distinct Shifts in Nutrient Transporter Expression, The Journal of Immunology, 2013, 190: 6043-6050.
Lin et al. Air-Liquid Interface (ALI) Culture of Human Bronchial Epithelial Cell Monolayers as an In Vitro Model for Airway Drug Transport Studies, J Pharm Sci 96:341-350, 2007.
Makam et al. Activation of critical, host-induced, metabolic and stress pathways marks neutrophil entry into cystic fibrosis lungs, Proc Natl Acad Sci U S A. 2009, 106(14):5779-83.
Mansour et al. Nanomedicine in pulmonary delivery, International Journal of Nanomedicine 2009:4 299-319.
Margaroli et al. Neutrophil plasticity enables the development of pathological microenvironments: implications for cystic fibrosis airway disease, Molecular and Cellular Pediatrics (2016) 3:38.
Mitchell, A GRIM fate for human neutrophils in airway disease, J Leukoc Biol. 2018, 104:657-659.
Punde et al. A 3-D capillary-endothelium-mimetic microfluidic chip for studying the extravasation behaviour of neutrophils, 2011 16th International Solid-State Sensors, Actuators and Microsystems Conference, 2011, pp. 2251-2254.
Roghanian et al. Neutrophil Elastase (NE) and NE Inhibitors: Canonical and Noncanonical Functions in Lung Chronic Inflammatory Diseases (Cystic Fibrosis and Chronic Obstructive Pulmonary Disease) Journal of Aerosol Medicine and Pulmonary Drug Delivery, vol. 21, No. 1, 2008, 125-144.
Ross et al. Transcriptional Profiling of Mucociliary Differentiation in Human Airway Epithelial Cells, Am J Respir Cell Mol Biol vol. 37. pp. 169-185, 2007.
Tirouvanziam et al. Profound functional and signaling changes in viable inflammatory neutrophils homing to cystic fibrosis airways, Proc Natl Acad Sci U S A. 2008, 105(11):4335-9.
Tirouvanziam et al. An Integrative Approach for Immune Monitoring of Human Health and Disease by Advanced Flow Cytometry Methods, Chapter 12, Advanced Optical Flow Cytometry: Methods and Disease Diagnoses, First Edition. 2011.
Ullmer et al. Respiratory virus infection of differentiated primary bronchial/tracheal and small airway epithelial cells, ATCC, (2007).

* cited by examiner

DEVICES AND METHODS RELATED TO AIRWAY INFLAMMATION

CROSS-REFERENCE TO RELATED APPLICATIONS

This application is a continuation of U.S. patent application Ser. No. 14/913,543 filed Feb. 22, 2016 that granted as U.S. Pat. No. 10,670,594 on Jun. 2, 2020, which is the National Stage of International Application No. PCT/US2014/052048 filed Aug. 21, 2014, which claims priority to U.S. Provisional Application No. 61/868,722 filed Aug. 22, 2013. The entirety of each of these applications is hereby incorporated by reference for all purposes.

BACKGROUND

Cystic Fibrosis (CF) is a life threatening recessive condition caused by mutations in the gene coding for the CF Transmembrane conductance Regulator (CFTR) protein. CFTR is expressed chiefly by exocrine epithelia, and its dysfunction in CF patients leads to abnormal ion balance, hydration, pH, and redox properties of exocrine secretions leading to organ disease. Hallmarks of CF airway disease include bronchiectasis, inflammation by polymorphonuclear neutrophils (PMNs) from blood, obstruction by mucus, and infection by bacteria. Airway disease is the main cause of morbidity in CF, starting after birth and progressing at a different pace depending on patients, leading to lung failure. Thus, there is a need to identify improved treatments.

The CFTR protein is a channel for small anions and a regulator of various other transport mechanisms that is expressed chiefly in exocrine epithelia. In the airways, defective CFTR function hampers the reabsorption of luminal glucose and amino acids by the epithelium, driving microbial growth and auxotrophic adaptation. The CF airway epithelium also secretes high levels of pro-inflammatory mediators, even in the absence of overt infection, leading to the recruitment of blood PMNs. Recruited PMNs produce reactive oxygen species (ROS) and release granule enzymes, e.g., myeloperoxidase (MPO), neutrophil elastase (NE), and matrix metalloprotease-9 (MMP-9) which lead to local production of highly active ROS, tissue proteolysis, high luminal amino acid levels, and changes in epithelial cells and glands. NE itself is a highly active protease and can reprogram epithelial cells and glands. Reflecting on its multiple pathological activities, NE activity in the airway fluid has been identified as a strong predictor of declining CF lung function.

Tirouvanziam et al. report functional and signaling changes in viable inflammatory neutrophils homing to cystic fibrosis airways. Proc Natl Acad Sci USA, 2008, 105(11): 4335-9. Makam et al. report activation of critical, host-induced, metabolic and stress pathways marks neutrophil entry into cystic fibrosis lungs. Proc Natl Acad Sci USA, 2009, 106(14):5779-83. Laval et al. report metabolic adaptation of neutrophils in cystic fibrosis airways involves distinct shifts in nutrient transporter expression. J Immunol, 2013, 190(12):6043-50.

Hibbert et al. report a method of transporting epithelial cell monolayers. US Application Publication 2010-0047907

Karp et al. report an in vitro model of differentiated human airway epithelia cells. Methods Mol Med, 2002, 188:115-137. Fulcher et al. report human airway epithelial cell cultures. Methods Mol Med, 2005, 107:183-206.

SUMMARY

This disclosure relates to devices, assays, and methods related to airway inflammation caused by polymorphonuclear neutrophils (PMNs). In certain embodiments, the disclosure relates to a model device that emulates the changes in airway cell physiology due to transmigration of PMNs from blood to the apical aspect of the cells grown at air-liquid interface (ALI). In certain embodiments, the airway cells are supported on a collagen layer wherein the collagen layer is further supported by a porous polymer from which PMNs can migrate. In certain embodiments, the disclosure relates to the use of the model system to test compounds to identify drug candidates and diagnose subjects with airway-related diseases and conditions.

In certain embodiments, the disclosure relates to devices used to evaluate airway cells. Typically the devices comprise: a layer of collagen between a first compartment and a second compartment; cells on the layer of collagen inside of the first compartment, wherein the cells are airway cells; and a porous layer next to the layer of collagen inside the second compartment, configured with a pore size sufficient for the transmigration of PMNs through the collagen layer, wherein the second compartment comprises a sample comprising PMNs configured to contact the porous layer.

In certain embodiments, the disclosure relates to methods comprising, contacting a solution with the layer of airway cells contained in devices as reported herein wherein said solution induces the PMNs in the second compartment to migrate to the first compartment; collecting a sample from the first compartment comprising transmigrated PMNs; and analyzing the transmigrated PMNs for a physical property.

In certain embodiments, the disclosure relates to methods of drug screening by testing a compound for treating PMN-mediated airway inflammation by adding a test compound into the first and/or second compartment(s) and identifying changes to the physical properties of the transmigrated PMNs compared to a simulated normal and/or diseased state or condition.

In certain embodiments, the disclosure relates to methods of predicting, aiding or assisting in the diagnoses, determining the risk of, monitoring the progression, or identifying candidate agents for treatment of a subject with an airway-related disease or condition.

BRIEF DESCRIPTION OF THE DRAWINGS

FIGS. 1A-D show data on PMN hyperexocytosis in chronic and early CF.

FIGS. 2A-B show data on caspase-1 and pinocytic activities in CF airway PMNs.

FIGS. 3A-C illustrate an in vitro model recapitulating CF small airway PMN inflammation.

FIGS. 5A-C show data indicating CF airway fluid supernatant (ASN) induces PMN reprogramming in the model system.

FIGS. 7A-B show an embodied device of the disclosure in the form of a plate array—FIG. 7A is a side view and the FIG. 7B is a top view. The device comprises a housing (3) configured to form a first compartment (1) and a second compartment (2), wherein a layer of collagen (4) is between the first compartment (1) and the second compartment (2). Airway cells (5) are on the layer of collagen inside of the first compartment (1). A porous layer (6) is next to/below the layer of collagen inside the second compartment (2). The porous material is configured with a pore size sufficient for the migration of polymorphonuclear neutrophils (7) through the collagen layer. PMNs break down the collagen during transmigration. The device contains a plurality of wells, enabling multiplexed screening experiments (8).

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

A "subject" refers to a human, newborn, fetus, laboratory animal, or domestic pet.

As used herein, methods for "aiding diagnosis" or "assisting in diagnosis" both refer to methods that assist in making a clinical determination regarding the presence or progression of the disease or conditions, and may or may not be conclusive with respect to the definitive diagnosis.

As used herein, the term "predicting" refers to making a finding with notably enhanced likelihood of developing the disease or condition.

As used herein, the term "fluid lung sample" or "lung fluid" and the like, refer to a biological sample derived from or around the lung or trachea. Examples include bronchoalveolar lavage fluid and airway epithelial cell fluid. Examples of obtaining a fluid lung sample include by dilution of bronchial brushings, mucosal biopsies, thoracentesis, lavage, sputum induction, or spontaneous expectoration. In bronchoalveolar lavage, a solution is injected onto airway epithelial cells, e.g., in the lung, and suctioned out to collect cells lining the airways.

As used herein, "blood sample" encompasses a biological sample which is derived from blood obtained from an individual and can be used in a diagnostic or monitoring assay. The definition encompasses blood, plasma, and serum.

As used herein, a "reference value" can be an absolute value; a relative value; an average value; a median value, a mean value, or a value as compared to a particular control or baseline value. A reference value can be based on an individual sample or a large number of samples, such as from patients or normal individuals.

A "normalized measured" value refers to a measurement taken and adjusted to take background into consideration. Background subtraction to obtain total fluorescence is considered a normalized measurement. The background subtraction allows for the correction of background fluorescence that is inherent in the optical system and assay buffers.

The term "binding agent" refers to a molecule, preferably a proteinaceous molecule, that specific binds a target with a greater affinity than other molecules, e.g., is at least 10 times as great, but optionally 50 times as great, 100, 250, or 500 times as great, or even at least 1000 times as great as the affinity of another antibody, peptide, or polypeptide of a random sequence of similarly size and overall hydrophobicity. Typically the specific binding agent is an antibody, such as a polyclonal or monoclonal antibody (mAb), single chain antibody, or fragments; however, other protein and non-protein based binging agents are contemplated such as, affibody molecules, affilins, affitins, anticalins, avimers, DARPins, fynomers, Kunitz domain peptides, monobodies, known or unknown, naturally occurring or synthetic ligands, receptors, or fragments thereof. Identifying a binding agent is routine to a skilled artisan, e.g., by screening a target molecule in a phage display, yeast display, bacterial display, ribosome display, or mRNA display library. See Miersch et al, Methods, 2012, 57(4):486-98. Screening small molecule libraries produced by combinatorial solid phase synthesis is also a method for identifying binding agents. See Made et al., Beilstein J Org Chem, 2014, 10:1197-212.

Devices and Methods of Use

In certain embodiments, the disclosure relates to devices used to evaluate airway cells. Typically the devices comprise a layer of collagen between a first compartment and a second compartment; cells on the layer of collagen inside of the first compartment, wherein the cells are airway cells; and a porous layer next to the layer of collagen inside the second compartment, configured with a pore size sufficient for the migration of PMNs through the collagen layer, wherein the second compartment comprises a sample comprising PMNs configured to contact the porous layer.

Typically, the layer of cells is airway cells, however, other cell types such as intestinal epithelial cells, stem cells or pluripotent cells are contemplated. In certain embodiments, the airway cells are human or non-human diseased or normal cells such as cystic fibrosis (CF) airway cells, non-CF bronchiectasis airway fluid, chronic obstructive pulmonary disease (COPD) airway cells, asthmatic airway cells, diabetic airway cells, bronchial smooth muscle cells, lung microvascular endothelial cells, bronchial tracheal epithelial cells, lung fibroblasts, pulmonary artery cells, small airway epithelial cells.

In certain embodiments, the disclosure relates to a device having a housing configured to form a first compartment and a second compartment; a layer of collagen between the first compartment and the second compartment; cells on the layer of collagen inside of the first compartment; and a porous layer next to the layer of collagen inside the second compartment, configured with a pore size sufficient for the migration of PMNs through the collagen layer. Typically, the second compartment comprises a sample comprising PMNs configured to contact the porous layer such as a blood sample.

In certain embodiments, the collagen layer is reconstituted from a powder that was the result of extraction from a natural source such as demineralized bond, tail, tendon, of rats, cows, humans or other animals. In one embodiment, the collagen layer is reconstituted from an acid extracted human placenta type I collagen.

In certain embodiments the porous layer is a biocompatible or inert polymer. In certain embodiments the porous layer contains polystyrene. The pores may be created by drilling holes through the polystyrene polymer or by the creation of a polymer matrix. In certain embodiments, the porous layer is Alvetex® which is a polystyrene scaffold typically with a thickness of about 200 microns. It has varying pore sizes, the majority about 36-40 microns. In certain embodiments the porous layer has a thickness between 150-250 microns. In certain embodiments, the porous layer comprises pores between 5 and 50 microns.

In certain embodiments, the first compartment comprises lung fluid obtained from a subject diagnosed, at risk of, exhibiting symptoms, or suspected of having an airway disease or condition wherein the lung fluid is configured to contact the airway cells in the device to induce transmigration of PMNs in the second compartment.

In certain embodiments, the device is arranged in a well of a substrate wherein said substrate houses a plurality of wells each comprising the first and second compartments described above. The number of wells can be between 5 and 100, or 96, or 2 and 1000, or more. In certain embodiments, the substrate housing is glass, metal, plastic, or combinations thereof.

As used herein, "collagen" refers to a material containing collagen fibril aggregates made up of three polypeptide strands in a helix, sometimes called tropocollagen. There is a predominant sequence pattern of three amino acids, two of which are predominately glycine and proline (or hydroxypoline) wherein the third may be any of various other amino acid residues. Glycine typically accounts for about a third of the sequence. Proline or hydroxyproline typically accounts for about one sixth of the total sequence. Differences in the primary structure (amino acid sequence) establish differences between the different types of collagen, e.g., collagen I, II, III, IV, etc. In the natural biochemical processes of forming collagen, hydroxylation of lysine and proline amino acids sometimes occurs which also allows for their glycosylated. Type I collagen is a natural component of skin, bone, tendon, placenta, and other fibrous connective tissues.

Collagen may be extracted from natural products in the presence of protein degrading enzymes such as pepsin and reconstituted. A threshold number of lysine residues in collagen allow for water solubility in acidic conditions varying on the acidity of the solution and the extent of lysine substitution. Acidic extraction followed by dehydration, e.g., lyophilization, typically results in a collagen powder. For example, see Niyibizi et al., J. Biol. Chem., 259:14170 (1984) for a process of obtaining collagen from human placenta. The acid soluble collagen powder can be dissolved in water with acetic acid to form gels of collagen. Dehydration of the gels and be configured to form a collagen layer, sheet, or film. In certain embodiments, a layer of collagen reconstituted from acid soluble extraction is applied on the porous layers.

In certain embodiments, the disclosure contemplates the use of reconstituted collagen that is dissolved in an aqueous acidic acid solution and applied directly on a porous polystyrene material under conditions to form a gel or film. In certain embodiments, the collagen is type I collage extracted from human placenta; however, other forms of collagen are contemplated. Reconstituted collagen sheets typically are able to absorb fluid.

Crosslinking agents may be used to form a covalent bridge between lysine residues within collagen. By introducing lysine into a protein structure on can added additional proteins by molecular crosslinking to collagen.

In certain embodiments, the disclosure relates to methods comprising, contacting a solution with the layer of airway cells contained in devices as reported herein wherein said solution induces the PMN cells in the second compartment to migrate to the first compartment; collecting a sample from the first compartment comprising transmigrated PMNs; and analyzing the transmigrated PMNs for a physical property.

In certain embodiments, the solution is an airway fluid is obtained from a subject diagnosed, at risk of, exhibiting symptoms, or suspected of having an airway disease or condition. In certain embodiments, solution is airway fluid obtained from a subject diagnosed with, CF, non-CF bronchiectasis, COPD, or asthma.

In certain embodiments, adding bacteria, fungi and/or viruses to the first and/or second compartment are done to allow modelling along various paths to emulate different disease states.

In certain embodiments, alternative sources of the collagen supported cells in the first compartment and PMNs are contemplated. In certain embodiments, the cells are airway epithelium, small airway cells (from bronchioles) a genetically engineered H441 cell line with a specific knock-out (e.g., of the cftr or beta-enac gene) and/or knock-in (e.g., expression of a specific cftr mutant) gene, other Clara cell lines (human or other species), primary bronchiolar epithelial cells from commercial or academic sources, large airway cells (from trachea and bronchi), matched primary cells expressing wild-type and KO or mutant cftr (e.g., 16HBE and CFBE, NuLi and CuFi lines (U of Iowa), primary bronchial epithelial cells from commercial or academic sources. In certain embodiments, the cells are intestinal epithelium such as Caco-2 and T84 cell lines with specific knock-out and/or knock-in genes.

In certain embodiments, the airway fluid is from subjects with chronic airway diseases such as non-CF bronchiectasis, COPD, asthma (both allergic and non-allergic asthma have a predominance of PMNs in the lamina propria and lumen, having also eosinophils represented, from lung transplant patients). CF being the major indication for lung transplantation, this source of fluid allows one to look at the impact of the in vivo replacement of CF lungs by normal lungs on the PMN reprogramming properties of the airway fluid. In certain embodiments, the airway fluid is from conditioned media from airway or PMN cultures or conditioned media from viral, bacterial or fungal cultures, with or without live organisms.

In certain embodiments, the PMNs are from human subjects with various conditions such as airway diseases, e.g., CF, non-CF bronchiectasis, COPD, asthma or subjects with primary immunodeficiencies, e.g., chronic granulomatous disease (CGD), Familial mediterranean fever (FMF), alpha-1 antitrypsin deficiency (A1AT).

In certain embodiments, the PMNs are from other species wild-type and knockout and/or knock-in mice, as a means to dissect out pathways key to PMN responsiveness to cues present in the fluid or Rhesus PMNs, as a means to document evolutionary changes in PMN responsiveness in comparison with human and mouse PMNs, or innate cell subsets such as eosinophils, which play an effector role in asthma and macrophages, which play a regulatory role in CF, non-CF bronchiectasis, COPD, and asthma.

In certain embodiments, analyzing the transmigrated PMN cells for a physical property is mixing the transmigrated PMNs with an antibody, binding agent, or other molecular probe that upon binding and detection indicates cell viability, apoptosis, pinocytosis, pro-inflammatory activity, or oxidative activity.

In certain embodiments, the physical property is the expression of surface markers on the surface of the transmigrated PMN cells, or expression of a polypeptide, enzyme, or nucleic acid within the transmigrated PMNs.

In certain embodiments, the physical property is internalization of a fluorescent molecule, such as Luciferase Yellow, into the transmigrated PMNs. In certain embodiments, analyzing the transmigrated PMN cells for a physical property is mixing the transmigrated PMN cells with Lucifer Yellow.

In certain embodiments, analyzing the transmigrated PMN cells for a physical property is mixing the transmigrated PMN cells with an antibody or other binding agent that binds to a cell surface marker wherein the antibody or binding agent is conjugated to a fluorescent molecule or the antibody or binding agent is made fluorescent thereafter, and separating antibody or binding agent bound transmigrated PMN cells by flow cytometry.

In certain embodiments, the surface marker is selected from CD45, CD3, CD14, CD16, CD33, CD63 and CD66b or combinations thereof.

In certain embodiments, analyzing the transmigrated PMN cells for a physical property is mixing the transmigrated PMN cells with a molecular probe that binds with active caspase-1. See Smolewski et al., Detection of caspase activation by fluorochrome-labeled inhibitors: multiparameter analysis by laser scanning cytometry. Cytometry 44:73-82 (2001). In certain embodiments, the probe is a fluorochrome-labeled inhibitor of caspase activation (FLICA). FLICA ligands are carboxyfluorescein (FAM)-labeled peptide fluoromethyl ketones (FMK). FMK moiety interacts with the cysteine of the active center to form a thiomethyl ketone and irreversibly inactivates the enzyme. The specificity of binding is provided by the sequence of amino acids in the tetrapeptide (e.g., VEID) moiety. The fluorescent tag (carboxyfluorescein, FAM) is located on the other end of the FLICA molecule.

Flow cytometry is a laser-based technique that may be employed in counting, sorting, and detecting cells by suspending particles in a stream of fluid and passing them by an electronic detection apparatus. A flow cytometer has the ability to discriminate different particles on the basis of color. Differential dyeing of particles with different dyes, emitting in two or more different wavelengths allows the particle to be distinguished. Multiplexed analysis allows one to perform multiple discrete assays in a single tube with the same sample at the same time.

In one example, particles may be beads each with distinctive combinations of fluorophores that confer each bead a specified, unique color code. Beads act as a solid surface that is coated with capture antibodies of interest. The bead can be mixed with an epitope, e.g., cell surface marker, providing a bead that is conjugated through an antibody to a cell of interest. Additional detection antibodies (fluorescent or made fluorescent for a reporter signal) can create a multicolored bead-cell complex. The beads are passed through a flow cell, on a laser instrument that utilizes two-laser system, in which one laser detects the color code of each bead, and the second laser detects the reporter signal, hence cells concentration.

In certain embodiments, the particles may be polystyrene microspheres that bear carboxylate functional groups on the surface. The particles can be covalently coupled to amine-containing ligands or antibodies to a surface marker through surface carboxylate groups; alternatively, avidin-coupled particles can be used for binding biotinylated ligands or antibodies. The bound cell can be exposed to fluorescent antibodies or nucleic acid detection reagents to provide a specific signal for each reaction in a multiplexed assay. Each fluorescent detection reagent binds specifically to a cell surface marker that is present on only one bead set in a multiplexed assay. Fluorescent molecules may be labeled with a green-emitting fluorophore such as Bodipy® (Molecular Probes) or fluorescein isothiocyanate.

In certain embodiments, the disclosure contemplates individual sets of particles of fluorescently coded particles conjugated with ligands or antibody to PMN surface markers. After mixing the particles with a sample, the particles are mixed with fluorescent detection antibodies or any fluorescent molecule that will bind to the surface markers. Mixtures of particles containing various amounts of fluorescence on their surfaces are analyzed with a flow cytometer. Data acquisition, analysis, and reporting are performed on the particles sets. As each particle is analyzed by the flow cytometer, the particle is classified into its distinct set on the basis fluorescence and values are recorded.

The data generated by flow cytometers can be plotted in a single dimension, to produce a histogram, or multi-dimensional plots, e.g., when multiple fluorescent moieties are attached or contained within the same cells. For example, it is specifically contemplated that antibodies to CD63 and CD16 and other probes disclosed herein can be conjugated with or made fluorescent with differing fluorescent moieties allowing the multi-dimension evaluation of PMN cells by flow cytometry. The regions on these plots can be sequentially separated, based on fluorescence intensity, by creating a series of subset extractions, termed "gates." For example, antibodies to CD45, CD3, CD14, CD16, CD33, CD63 and CD66b for can be used for gating of PMNs obtained from blood and lung fluid samples (BALF), e.g., $CD45^{lo}CD33^{hi}CD66b^{hi}CD63^{lo}CD16^{hi}$ as A1 subset;
$CD45^{lo}CD33^{hi}CD66b^{hi}CD63^{hi}CD16^{lo}$ as A2 subset;
$CD45^{hi}CD33^{hi}CD66b^-$ as monocytes/macrophages;
$CD45^{hi}CD3^+$ as T-cells;
$CD45^{hi}CD33^{hi}CD66b^{hi}CD16^-$) as eosinophils;
$CD45^{hi}CD66b^-CD16^+$ as NK cells; and
$CD45^{hi}CD3^-CD33^-CD66b^-CD16^-$ as B-cells.

Non-antibody based probes can be used for gating viability (Live/Dead), apoptosis (Annexin V), pinocytosis (Lucifer Yellow uptake), pro-inflammatory activity (caspase-1) and oxidative activity (ROS). Multiple functional outcomes can be measured simultaneously on blood and lung fluid subsets. It is also contemplated that PMNs can be mixed with fluorescent bacteria to assess their phagocytic ability.

Another contemplated test setup for determining physical properties of PMN cells disclosed herein include the use of an immune assay, a radioimmunoassay, or a ligand binding assay, e.g., enzyme-linked immunosorbent assay. The cell is immobilized on a solid support such as a polystyrene microtiter plate either non-specifically by adsorption to spots or zones on the surface or specifically by capture by a ligand—molecule that has affinity for the cell, e.g., antibody specific to the cell surface maker. After the biomarker is immobilized presence of the cells is detected. In one example, a detection antibody (e.g., second antibody) is mixed with the surface. If the biomarker is in the spot, the detection antibody may form a complex with the cell. The detection antibody may be covalently linked to an enzyme that creates a signal upon exposure to appropriate conditions, e.g., by adding an enzymatic substrate to produce a visible signal which indicates the quantity of antigen in the sample. The detection antibody may be itself detected or monitored by a variety of techniques, such as through an antibody with affinity for the detection antibody conjugated to an enzyme. Typically the surface is washed to remove any cells that are not specifically bound.

In certain embodiments, the cells can be immobilized on the surface by ligand binding and a detection reagent will bind specifically to a cells surface marker. The detection reagent may be conjugated to an enzyme to generate a signal that can be quantified. For example, Rica & Stevens report an enzyme label that controls the growth of gold nanoparticles and generates colored solutions with distinct tonality when the analyte is present. See Nature Nanotechnology, 7:821-824 (2012).

In certain embodiments, the cells are captured with a ligand or antibody on a surface and the cells is labeled with an enzyme. In one example, a detection antibody conjugated to biotin or streptavidin—to create a biotin-streptavidin linkage to on an enzyme that contains biotin or streptavidin. A signal is generated by the conversion of the enzyme substrate into a colored molecule and the intensity of the color of the solution is quantified by measuring the absorbance with a light sensor. Contemplated assays may utilize chromogenic reporters and substrates that produce some kind of observable color change to indicate the presence of the cell. Fluorogenic, electrochemiluminescent, and real-time PCR reporters are also contemplated to create quantifiable signals.

Drug Screening

In certain embodiments, the disclosure relates to methods of drug screening by testing a compound for treating PMN airway inflammation by adding a test compound into the first or second compartments and identifying changes to the physical properties of the transmigrated PMNs compared to a simulated normal and/or diseased state or condition.

In certain embodiments, the disclosure relates to methods of testing a compound for treating PMN-associated airway inflammation comprising, contacting a solution with the layer of airway cells contained in a device of as reported herein, wherein said solution is capable of inducing the PMNs in the second compartment to migrate to the first compartment providing transmigrated PMNs, and said solution is capable of inducing the transmigrated PMNs to increase release of NE and MPO, increase caspase-1, increase expression of CD63 and decreased expression of CD16 on said cells; contacting a test compound with the layer of airway cells; collecting a sample from the first compartment comprising transmigrated PMNs; and analyzing the transmigrated PMNs to determine whether the test compound reduced the ability of the solution to induce the transmigrated PMNs to increase release of NE and MPO, increase caspase-1, increase expression of CD63, or decreased expression of CD16 on said cells.

In certain embodiments, the disclosure relates to methods of testing a compound for treating PMN-associated airway inflammation comprising, contacting a solution with the layer of airway cells contained in a device as reported herein, wherein said solution is capable of inducing the PMNs in the second compartment to migrate to the first compartment providing transmigrated PMNs, and said solution is capable of inducing the transmigrated PMNs to increase release of NE and MPO, increase caspase-1, increase expression of CD63 and decreased expression of CD16 on said cells; contacting a test compound with the PMNs in the second compartment; collecting a sample from the first compartment comprising transmigrated PMNs; and analyzing the transmigrated PMNs to determine whether the test compound reduced the ability of the solution to induce the transmigrated PMN cells to increase release of NE and MPO, increase caspase-1, increase expression of CD63 or decreased expression of CD16 on said cells.

In certain embodiments, the disclosure relates to methods of testing a compound for treating PMN-associated airway inflammation comprising, contacting a solution with the layer of airway cells contained in a device as reported herein, wherein said solution is capable of inducing the PMNs in the second compartment to migrate to the first compartment providing transmigrated PMNs, and said solution is capable of inducing the transmigrated PMNs and cause decay, death, or reduced functioning of the airway cells; contacting a test compound with the layer of airway cells; and analyzing the airway cells to determine whether the test compound reduced the ability of the solution to cause decay, death, or reduced functioning of the airway cells.

In certain embodiments, the disclosure relates to methods of testing a compound for treating PMN airway inflammation comprising, contacting a solution with the layer of airway cells contained in a device as reported herein, wherein said solution is capable of inducing the PMNs in the second compartment to migrate to the first compartment providing transmigrated PMNs, and said solution is capable of inducing the transmigrated PMNs and cause decay, death, or reduced functioning of the airway cells; contacting a test compound with the PMNs in the second compartment; and analyzing the airway cells to determine whether the test compound reduced the ability of the solution to cause decay, death, or reduced functioning of the airway cells.

Diagnostic Methods

In certain embodiments, the disclosure relates to methods of predicting, aiding or assisting in the diagnoses, determining the risk of, monitoring the progression, or identifying candidate agents for treatment of a subject with an airway disease or condition. In certain embodiments, the disclosure provides methods for monitoring progression of an airway disease or conditions by evaluation of PMNs subject with devices and methods disclosed herein providing measured levels of PMN populations or markers, e.g., CD63, CD16 and other surface proteins, caspase-1 and other intracellular enzymes, nucleic acids and making comparisons to reference levels or previous test results. In the case of monitoring disease progression one, two, or more samples, may be analyzed daily, weekly, monthly, bimonthly, biannually, or annually. In certain embodiments, the subject has been diagnosed with an airway disease, e.g., the subject has been diagnosed with CF due to abnormal sweat chloride levels, raised blood concentrations of immunoreactive trypsinogen or mutated copies of the Or gene.

In certain embodiments, the disclosure relates to methods comprising: obtaining an airway fluid sample from a subject; contacting the airway fluid sample with the layer of airway cells contained in a device as reported herein wherein said airway fluid sample is capable of inducing the PMNs in the second compartment to migrate to the first compartment providing transmigrated PMNs, determining whether the transmigrated PMNs indicate an airway disease state.

In certain embodiments, determining is performed by contacting a sample of the transmigrated PMNs with antibody to CD63 or CD16 and detecting whether binding occurs between the transmigrated PMNs and the antibody to CD63 or CD16 using flow cytometry; diagnosing the patient as having an airway disease if there is an increase expression of CD63 or decreased expression of CD16 on said cells compared to normal PMNs or diagnosing the patient as not having an airway disease if there is an expression of CD63 or expression of CD16 on said cells that is similar to normal PMNs.

In certain embodiments, determining is performed by contacting a sample of the transmigrated PMNs with cell permeable probe that binds active caspase-1 and detecting whether binding occurs between caspase-1 in the transmigrated PMNs and the cell permeable probe using flow cytometry; diagnosing the patient as having an airway disease if there is an increased/altered expression of active caspase-1 compared to normal PMNs or diagnosing the patient as not having an airway disease if there is an expression of active caspase-1 in said cells that is similar to normal PMNs.

In certain embodiments, determining is performed by contacting a sample of the transmigrated PMNs with a fluorescent moiety that indicates pinocytic activity and detecting whether the fluorescent moiety is internalized in the transmigrated PMNs using flow cytometry; diagnosing the patient as having an airway disease if there is an increase internalization of the fluorescent moiety compared to normal PMNs or diagnosing the patient as not having an airway disease if there is an internalization of the fluorescent moiety in said cells that is similar to normal PMNs.

A physical property, e.g., surface marker expression, profile is considered "identified" as being useful for aiding in the diagnosis, diagnosis, stratification, monitoring, and/or prediction of airway disease when it is significantly different between the subsets of samples tested. Levels are "significantly different" when the probability that the property has been identified by chance is less than a predetermined value. The method of calculating such probability will depend on the exact method utilizes to compare the levels between the subsets. As will be understood by those in the art, the predetermined value will vary depending on the number the number of samples utilized. Accordingly, predetermined value may range from as high as 50% to as low as 20, 10, 5, 3, 2, or 1%.

The process of comparing a measured value and a reference value can be carried out in any convenient manner appropriate to the type of measured value and reference value for a physical property at issue. Measuring can be performed using quantitative or qualitative measurement techniques, and the mode of comparing a measured value and a reference value can vary depending on the measurement technology employed. For example, when a qualitative colorimetric assay is used to measure surface marker levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). As with qualitative measurements, the comparison can be made by inspecting the numerical data, by inspecting representations of the data (e.g., inspecting graphical representations such as bar or line graphs).

Examples

CF Airway PMNs

Figure 1A:
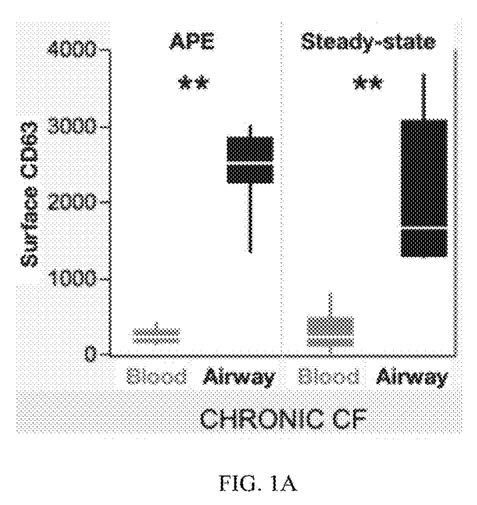
FIG. 1A and FIG. 1B show analysis during acute pulmonary exacerbations (APE) and at steady state show increased surface CD63 and decreased surface CD16 in CF airway vs. blood PMNs.
Figure 1B:
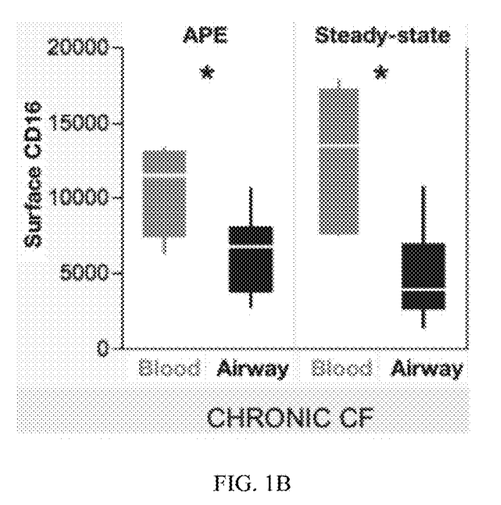
Figure 1C:
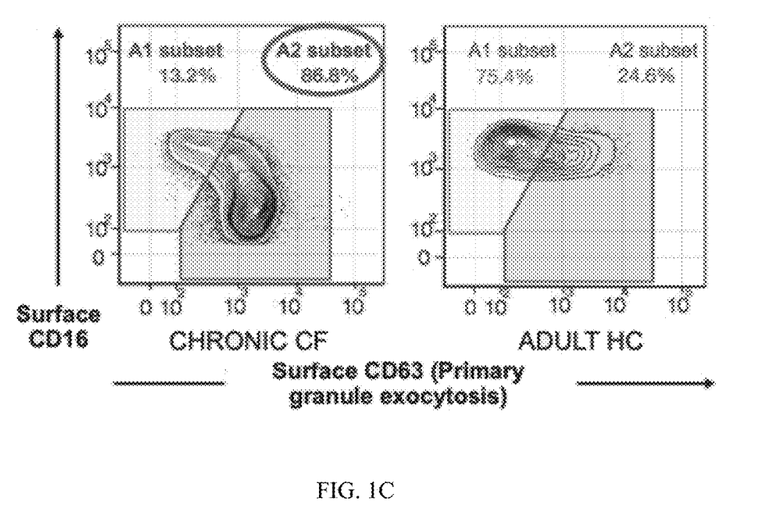
FIG. 1C shows airway PMNs in chronic CF patients, but not healthy controls (HC), are predominantly CD63hiCD16lo (designated as A2 subset).
Figure 1D:
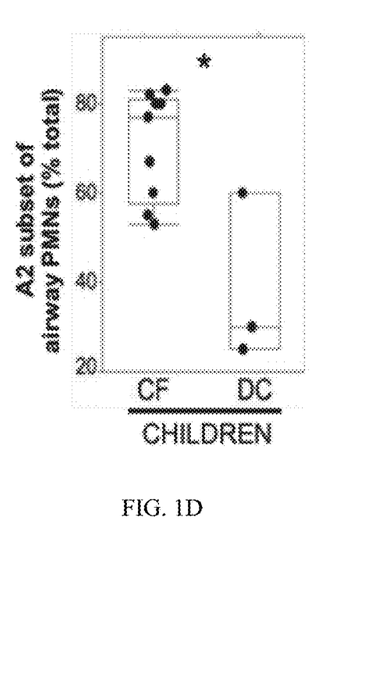
FIG. 1D shows in CF infants, the A2 subset of airway PMNs is very high compared to disease controls (DC). * and ** for P–0.05 and 0.01.

Hyperexocytosis of primary granules occurs in chronic and early CF airway disease. Using direct analysis of airway PMNs by cytometry, experiments indicate that NE and MPO release in CF stems in large part from hyperexocytosis by live PMNs. Data indicates that CF airway PMNs are characterized by high surface levels of CD63 (hyperexocytosis, FIG. 1A) and low surface levels of CD16 (reflecting loss of phagocytic receptor expression, FIG. 1B), such that live airway PMNs in chronic CF disease are primarily of the $CD63^{hi}CD16^{lo}$ phenotype (designated as "A2" subset), in contrast with the major $CD63^{lo}CD16^{hi}$ subset ("A1" subset) found in healthy control airways (FIG. 1C). Data also indicates that CF children (N=9, 3-40 months, with very mild disease and without any chronic infection) also showed a very high frequency of A2 PMNs in the airways (FIG. 1D). This suggests that PMN hyperexocytosis occurs early in CF pathogenesis.

Figure 2A:
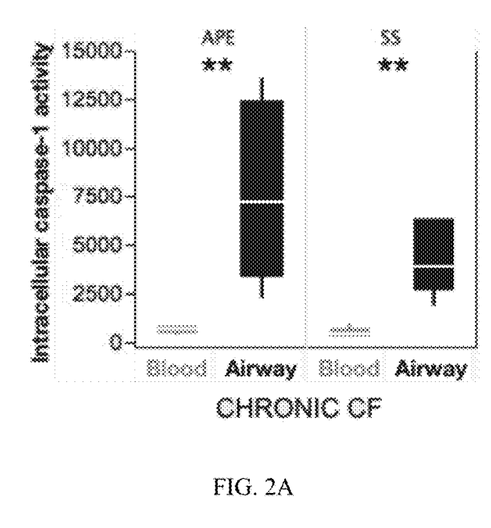
FIG. 2A shows analysis during acute pulmonary exacerbation (APE) and steady state (SS) show increased caspase-1 activity in live CF airway vs. blood PMNs, based on a cell-permeable probe binding the active site of the enzyme.
Figure 2B:
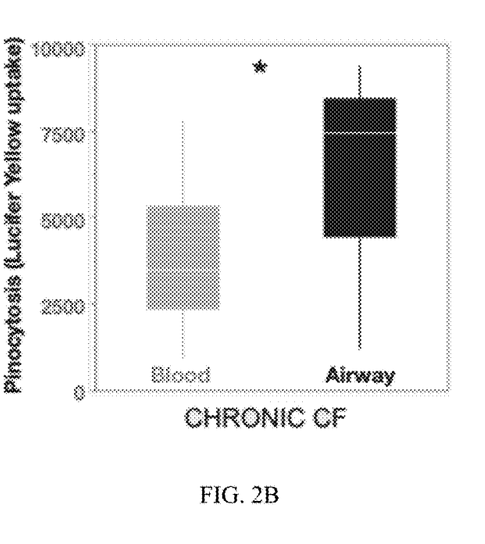
FIG. 2B shows airway PMNs in chronic CF (steady-state) show higher pinocytosis than blood PMNs, as measured by Lucifer Yellow uptake. * and ** indicate P<0.05 and 0.01, respectively.

CF airway PMNs show high pinocytic and caspase-1 activities. Using cytometry-based phenotyping, airway PMNs in chronic CF induce two activities, besides hyperexocytosis. First, they show high intracellular activity of caspase-1 (FIG. 2A), a non-apoptotic caspase that produces the pro-inflammatory mediator interleukin-1β (IL-1β). Consistently, high IL-1β levels in CF airway fluid were found. Second, CF airway PMNs show high pinocytic activity, based on Lucifer Yellow (LY) uptake (FIG. 2B).

Figure 3A:
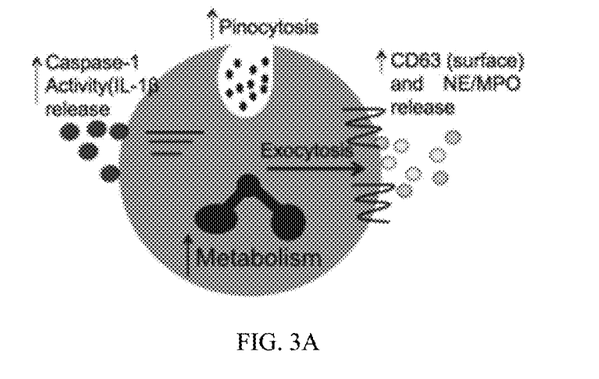
FIG. 3A illustrates primary granule release by airway PMNs in chronic CF disease which release NE and MPO as part of a reprogramming process that is characterized by the physical properties of high surface levels of CD63 (hyperexocytosis), low surface levels of CD16 (reflecting loss of phagocytic receptor expression), high intracellular activity of caspase-1, and high pinocytic activity.
Figure 3B:
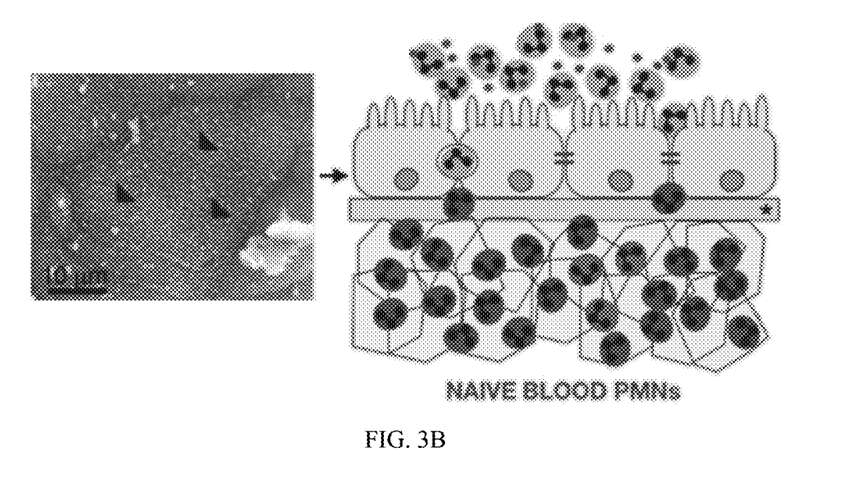
FIG. 3B illustrates a model of PMN-induced airway inflammation based on an ALI culture of H441 human small airway cells, with CF airway fluid used as the apical medium to induce the transmigration and reprogramming of naïve blood PMNs placed on the basal side.
Figure 3C:
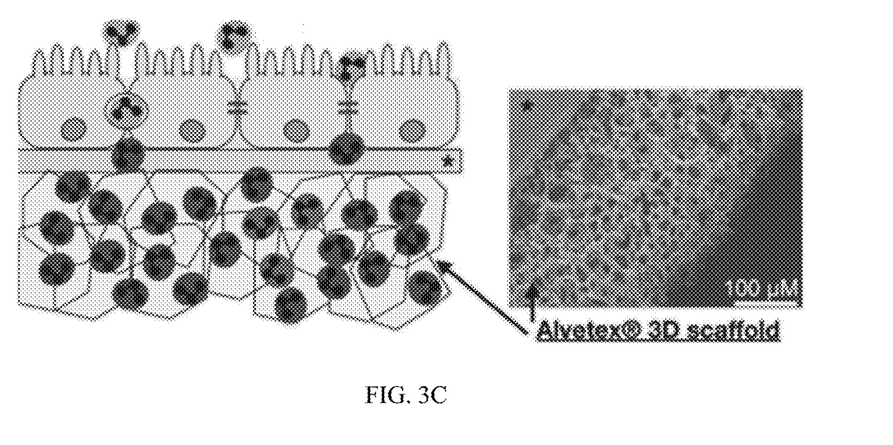
FIG. 3C illustrates that collagen (star) is on the Alvetex® scaffold which simulates the natural path for PMN transepithelial migration from the basal side to the apical side due to CF airway fluid or chemoattractants.

In Vitro Model Recapitulating the Pathological Process of CF Airway PMN Reprogramming Research on CF airway disease is often focused on large, gland-bearing airways (bronchi), which are a major site of disease. However, early signs of CF airway disease occur in the small airways (bronchioles). While multiple animal and in vitro models exist for large airways, those for small airways are rare. Disclosed herein is a setup for recapitulating PMN transmigration into small airways (FIG. 3).

Figure 4:
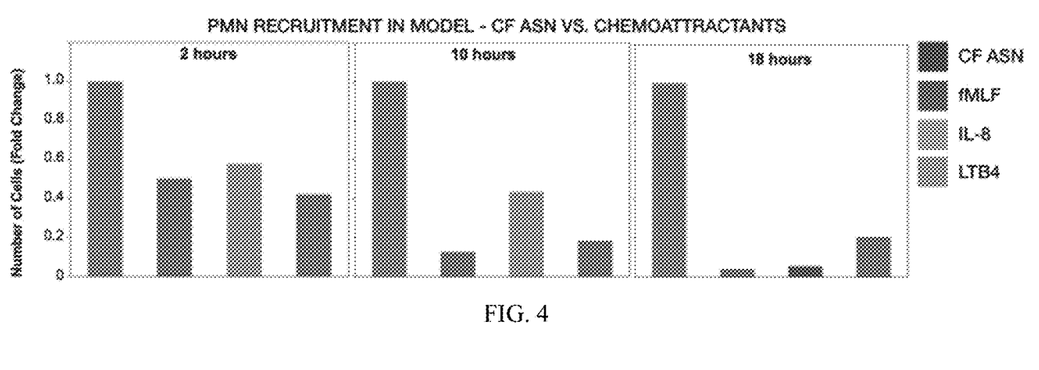
FIG. 4 shows data indicating CF airway fluid supernatant (ASN) is more potent that standard chemoattractants in recruiting PMNs in our transmigration model. Data normalized to the CF ASN condition. Note that the differential between CF ASN and fMLF, IL-8 and LTB4 increases with time due to increased survival in ASN.
Figure 5A:
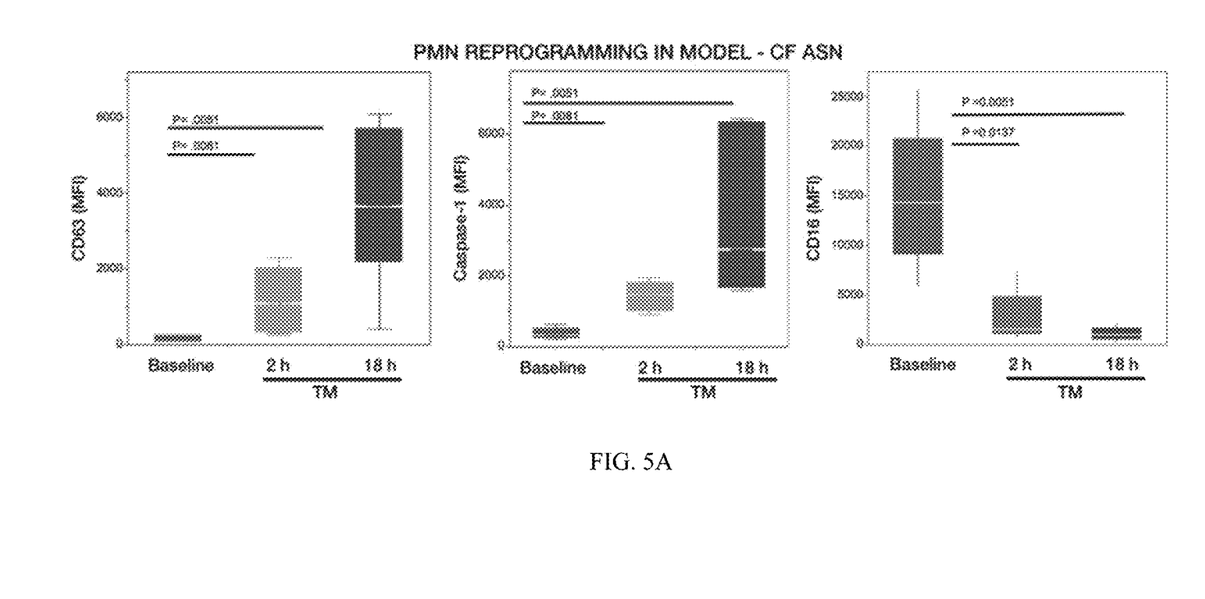
FIG. 5A shows CD63 (exocytosis) and caspase-1 (pro-inflammatory activity) are induced and CD16 (phagocytic receptor) decreased in PMNs transmigrated (TM) into CF ASN.
Figure 5B:
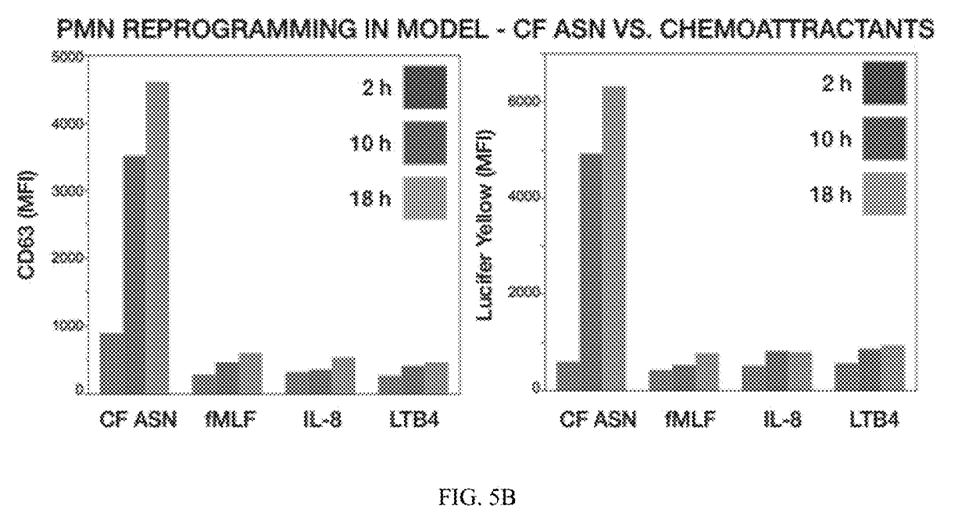
FIG. 5B shows chemoattractants do not induce PMN reprogramming, as judged by CD63 (exocytosis) and Lucifer Yellow (pinocytosis).
Figure 5C:
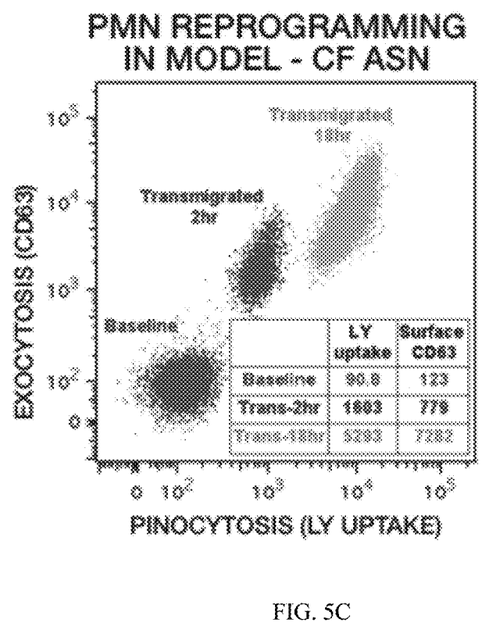
FIG. 5C shows exocytosis and pinocytosis are correlated during PMN reprogramming by CF ASN in vitro.

Since transmigration is a process in PMN conditioning, a unique air-interface small airway PMN transmigration model has been designed that phenocopies pro-exocytosis and pro-survival changes seen in vivo. This model integrates Clara-like cells, representative of the small airways believed to be affected during CF disease. Features in this model are independently controllable, including apical fluids, PMNs added to the basal side, and drugs added on either or both sides, which provide unique opportunities for mechanistic studies of the process of PMN-driven airway inflammation. This model provides the ability to study mechanisms and screen potential drug modulators of PMN-driven small airway inflammation, for example in CF. This platform has several elements: 1) a well-differentiated human small airway epithelial barrier maintained at air-liquid interface; 2); a porous support that emulates the structure of the small airway interstitium; 3) naive human blood PMNs, added to the basal side of the model; and 4) apical stimuli (bronchoalveolar lavage fluid (BALF), airway fluid rid of cells and bacteria, chemoattractants), added on top to recruit PMNs through the epithelial layer and into the lumen. When airway fluid from chronic CF patients is added apically, naive blood PMNs from healthy controls (or CF patients) are recruited into the lumen and develop strikingly similar features to those of CF airway PMNs in vivo. This model can be used to test a sample, e.g., BALF, from a subject suspected of having an airway lung disease for the ability to induce changes on PMNs. Chronic CF airway fluid alone (rid of cells and bacteria) can trigger PMN recruitment and reprogramming in this model. Chemoattractants used in lieu of CF airway fluid lead to lower recruitment and do not induce reprogramming. See FIGS. 4 and 5.

This model can also be used to test and assess drugs targeted at PMN reprogramming and on their ability to alter inflammation. While conventional HTS strategies focus on molecular entities, a strategy is to focus on this disease process (PMN transmigration and reprogramming), integrating target cells (PMNs) and the relevant milieu (CF airway fluid), and enabling drug testing in in vivo-like conditions.

In a typical experiment, the apical side will be bathed with CF airway fluid (positive control for transmigration and reprogramming), chemo-attractants (positive control for transmigration and negative control for reprogramming), or medium (negative control for both). Molecule for testing can be added to the basal side to test for systemic activity (by oral or intravenous administration) or can be combined with CF airway fluid to test for administrating through the lungs, e.g., administration by inhalation.

Analyses of PMNs collected in the model can be accomplished by using multiplexed flow cytometry, such that multiple endpoints of alteration of activity can be assessed simultaneously with a multi-color staining combination (compatible with automated plate cytometers). For live PMN gating testing may be based on scatter, Live/Dead negativity, and positivity for CD66b. For live PMN enumeration testing may be based absolute count using spiked counting beads. For exocytosis testing may be based surface CD63. For caspase-1 activity testing may be based intracellular staining with caspase-1 active site probe. For pinocytosis testing may be based on Lucifer Yellow uptake. With this integrated analytical scheme, viability and number of transmigrated PMN and key phenotypes linked to reprogramming can be assessed in a flow cytometry assay. In addition to this set of cell-based endpoints, confirmatory assays may be used to measure cell and fluid properties using image cytometry (to visualize pinocytic vesicles), Luminex (to measure secretion of caspase-1 derived cytokines), spectrometry (to measure NE and MPO release by exocytosis, and Lucifer Yellow decrease due to uptake), Western Blot (to measure cleavage and thereby activation of intracellular caspase-1) and transcriptomics (to assess transcriptional reprogramming in PMNs).

This model can be used for finding inhibitors of PMN-driven small airway inflammation in CF and other PMN-driven inflammation in other diseases and conditions, including, but not limited to non-CF bronchiectasis, chronic obstructive pulmonary disease (COPD) and neutrophilic asthma.

CF Airway PMNs are Metabolically and Transcriptionally Altered

Figure 6:
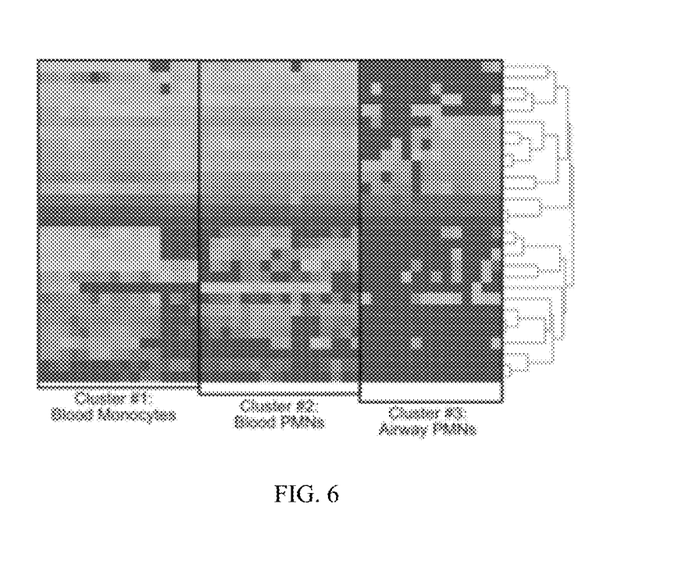
FIG. 6 shows data indicating transcriptional profiling of CF airway PMNs. Competitive hybridization microarray of blood and airway PMNs from patients reveals marked changes in transcription induced by recruitment to CF airways. Unsupervised clustering of Fluidigm data distinguished airway PMNs (right most cluster) from blood PMNs and monocytes.
Figure 7A:
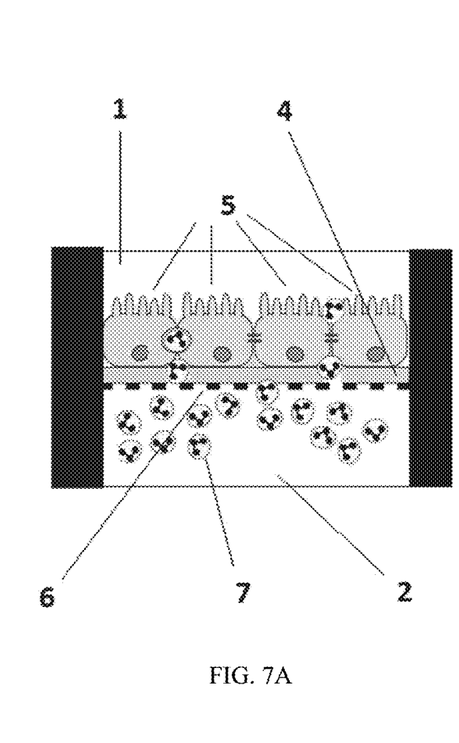
Figure 7B:
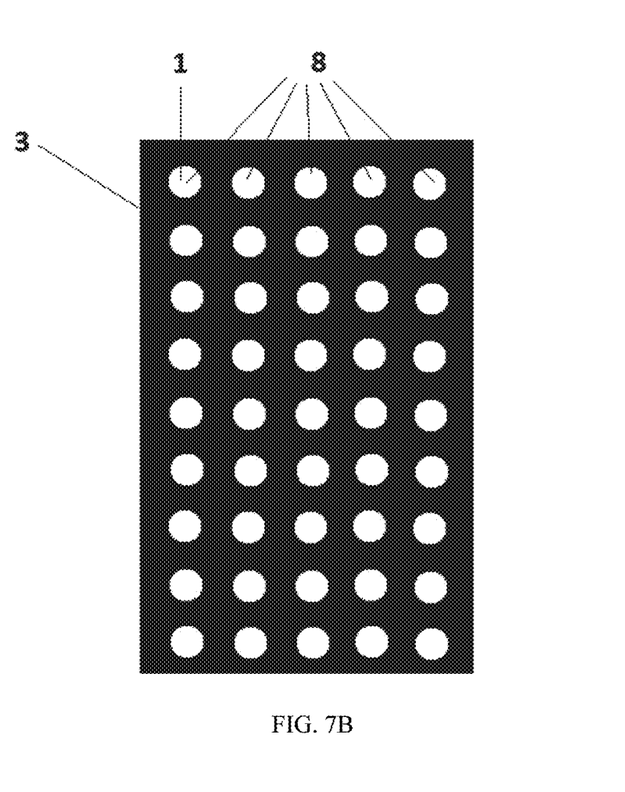

Airway PMNs in chronic CF trigger anabolic signaling along the mammalian target of rapamycin (mTOR) pathway and increase glucose, amino acid and phosphate transporter expression. To assess if metabolic changes were associated with transcriptional changes, sorted airway and blood PMNs were analyzed by microarrays. Changes in mRNA expression over 2-fold were seen in ~10% of genes. Gene Ontology analysis shows that: 1) downregulated mRNAs in CF airway PMNs relate to wound healing (p<10-13), programmed cell death (p<10-6), and phosphatase activity (p<10-2); and 2) upregulated mRNAs relate to translational elongation (p<10-94), ribosome formation (p<10-83) and cellular component biogenesis (p<10-10). Thus, PMNs inhibit death pathways and induce anabolic pathways while being activated in CF airways. To gain further insight into this question, the multiplexed qPCR Fluidigm platform was used as a profiling method as shown in FIG. 6. A chip was designed with 48 transcripts involved in signaling (mTOR, and other pathways relevant to CF airway PMNs), functional responses, and a chosen set of highly up/down-regulated mRNAs, per the microarray data. The mRNA data suggest that PMNs undergo key transcriptional changes in the CF airway lumen.

The invention claimed is:

1. A method of testing a compound for treating cystic fibrosis comprising, providing a device comprising
a layer of collagen between a first compartment and a second compartment;
cells on the layer of collagen inside of the first compartment, wherein the cells are human small airway epithelial cells; and
a porous layer next to the layer of collagen inside the second compartment configured with a pore size sufficient for the migration of polymorphonuclear neutrophils (PMNs) to the collagen layer and into the first compartment, wherein the second compartment comprises polymorphonuclear neutrophils (PMNs) in contact with the porous layer;
contacting human cystic fibrosis airway fluid comprising a test compound with the human small airway epithelial cells, wherein said human cystic fibrosis airway fluid in the absence of the test compound induces the PMNs in the second compartment to migrate to the first compartment containing the human cystic fibrosis airway fluid providing transmigrated PMNs, and said human cystic fibrosis airway fluid induces the transmigrated PMNs to increase release of NE and MPO, increase caspase-1 activity, increase expression of CD63 and decrease expression of CD16 in the transmigrated PMNs;
collecting a sample of the human cystic fibrosis airway fluid from the first compartment comprising transmigrated PMNs; and
analyzing the transmigrated PMNs to determine whether the test compound reduced the ability of the human cystic fibrosis airway fluid to induce the transmigrated PMNs to increase release of neutrophil elastase (NE) and myeloperoxidase (MPO), increase caspase-1 activity, increase expression of CD63, or decreased expression of CD16 in the transmigrated PMNs.

2. A method of testing a compound for treating cystic fibrosis comprising,
providing a device comprising
a layer of collagen between a first compartment and a second compartment;
cells on the layer of collagen inside of the first compartment, wherein the cells are human small airway epithelial cells; and
a porous layer next to the layer of collagen inside the second compartment configured with a pore size sufficient for the migration of polymorphonuclear neutrophils (PMNs) to the collagen layer and into the first compartment, wherein the second compartment comprises a test compound and polymorphonuclear neutrophils (PMNs) in contact with the porous layer;
contacting human cystic fibrosis airway fluid with the human small airway epithelial cells, wherein said human cystic fibrosis airway fluid in the absence of the test compound induces the PMNs in the second compartment to migrate to the first compartment containing the human cystic fibrosis airway fluid providing transmigrated PMNs, and said human cystic fibrosis airway fluid induces the transmigrated PMNs to increase release of NE and MPO, increase caspase-1 activity, increase expression of CD63 and decrease expression of CD16 in the transmigrated PMNs;
collecting a sample of the human cystic fibrosis airway fluid from the first compartment comprising transmigrated PMNs; and
analyzing the transmigrated PMNs to determine whether the test compound reduced the ability of the human cystic fibrosis airway fluid to induce the transmigrated PMNs to increase release of neutrophil elastase (NE) and myeloperoxidase (MPO), increase caspase-1 activity, increase expression of CD63, or decreased expression of CD16 in the transmigrated PMNs.

3. A method of testing a compound for treating cystic fibrosis, chronic obstructive pulmonary disorder, or asthma comprising,
providing a device comprising
a layer of collagen between a first compartment and a second compartment;
cells on the layer of collagen inside of the first compartment, wherein the cells are human small airway epithelial cells; and
a porous layer next to the layer of collagen inside the second compartment configured with a pore size sufficient for the migration of polymorphonuclear neutrophils (PMNs) to the collagen layer and into the first compartment, wherein the second compartment comprises polymorphonuclear neutrophils (PMNs) in contact with the porous layer;
contacting human PMN-driven inflammation airway fluid comprising a test compound with the human small airway epithelial cells, wherein said human PMN-driven inflammation airway fluid in the absence of the test compound induces the PMNs in the second compartment to migrate to the first compartment containing the human PMN-driven inflammation airway fluid providing transmigrated PMNs, and said human PMN-driven inflammation airway fluid induces the transmigrated PMNs to increase release of NE, increase expression of CD63 and decrease expression of CD16 in the transmigrated PMNs;
collecting a sample of the human PMN-driven inflammation airway fluid from the first compartment comprising transmigrated PMNs; and
analyzing the transmigrated PMNs to determine whether the test compound reduced the ability of the human PMN-driven inflammation airway fluid to induce the transmigrated PMNs to increase release of neutrophil elastase (NE), increase expression of CD63, or decreased expression of CD16 in the transmigrated PMNs.

4. A method of testing a compound for treating cystic fibrosis, chronic obstructive pulmonary disorder, or asthma comprising,
providing a device comprising
a layer of collagen between a first compartment and a second compartment;
cells on the layer of collagen inside of the first compartment, wherein the cells are human small airway epithelial cells; and
a porous layer next to the layer of collagen inside the second compartment configured with a pore size sufficient for the migration of polymorphonuclear neutrophils (PMNs) to the collagen layer and into the first compartment, wherein the second compartment comprises a test compound and polymorphonuclear neutrophils (PMNs) in contact with the porous layer;
contacting human PMN-driven inflammation airway fluid with the human small airway epithelial cells, wherein said human PMN-driven inflammation airway fluid in the absence of the test compound induces the PMNs in the second compartment to migrate to the first compartment containing the human PMN-driven inflammation airway fluid providing transmigrated PMNs, and said human PMN-driven inflammation airway fluid induces the transmigrated PMNs to increase release of NE, increase expression of CD63, and decrease expression of CD16 in the transmigrated PMNs;

collecting a sample of the human PMN-driven inflammation airway fluid from the first compartment comprising transmigrated PMNs; and analyzing the transmigrated PMNs to determine whether the test compound reduced the ability of the human PMN-driven inflammation airway fluid to induce the transmigrated PMNs to increase release of neutrophil elastase (NE), increase expression of CD63, or decreased expression of CD16 in the transmigrated PMNs.

\* \* \* \* \*